United States Patent
Beckman et al.

(10) Patent No.: US 7,264,823 B2
(45) Date of Patent: *Sep. 4, 2007

(54) MEDICAL ADHESIVE AND METHODS OF TISSUE ADHESION

(75) Inventors: Eric J. Beckman, Aspinwall, PA (US); Michael Buckley, Murrysville, PA (US); Sudha Agarwal, Allison Park, PA (US); Jianying Zhang, Pittsbugh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/361,431

(22) Filed: Feb. 10, 2003

(65) Prior Publication Data

US 2004/0170597 A1   Sep. 2, 2004

Related U.S. Application Data

(60) Provisional application No. 60/355,290, filed on Feb. 8, 2002.

(51) Int. Cl.
*A61F 13/02*   (2006.01)
*A61L 15/16*   (2006.01)

(52) U.S. Cl. .................................. 424/448; 424/445
(58) Field of Classification Search ................ 424/448, 424/445
See application file for complete search history.

(56) References Cited

U.S. PATENT DOCUMENTS

| 4,740,534 A | 4/1988 | Matsuda |
| 4,804,691 A | 2/1989 | English |
| 4,994,542 A * | 2/1991 | Matsuda et al. ............... 528/70 |
| 5,173,301 A * | 12/1992 | Itoh et al. .................... 424/448 |
| 5,674,921 A * | 10/1997 | Regula et al. ................. 522/97 |

FOREIGN PATENT DOCUMENTS

| EP | 0 466 552 | 1/1992 |
| JP | 63 278924 | 11/1988 |
| WO | WO 2004/009227 | 7/2002 |
| WO | PCT/US2004/016767 | 5/2004 |

OTHER PUBLICATIONS

Zhang et al., "A new peptide-based urethane polymer: synthesis, biodegradation, and potential to support cell growth in vitro," (2000), Biomolecules 21, 1247-1258.*

(Continued)

*Primary Examiner*—Carlos A. Azpuru
(74) *Attorney, Agent, or Firm*—Bartony & Hare, LLP

(57) ABSTRACT

An adhesive including a mixture of isocyanate capped molecules formed by reacting multi-isocyanate functional molecules with multi-functional precursor molecules including terminal functional groups selected from the group consisting of a hydroxyl group, a primary amino group and a secondary amino group. Preferably, the functional groups are hydroxyl groups. The multi-functional precursor compounds are biocompatible. Multi-amine functional precursors of the multi-isocyanate functional molecules are also biocompatible. As discussed, above, the mixture of molecules preferably has an average isocyanate functionality of at least 2.1 and, more preferably, has an average isocyanate functionality of at least 2.5. As also described above, the mixture of molecules preferably has a viscosity in the range of approximately 1 to approximately 100 centipoise. The mixture of molecules forms a crosslinked polymer network upon contact with the organic tissue in the presence of water. The crosslinked polymer network is biocompatible and biodegradable. The crosslinked polymer network degrades into degradation products including the precursor molecules and the multi-amine functional precursors.

6 Claims, 4 Drawing Sheets

OTHER PUBLICATIONS

See http://en.wikipedia.org/wiki/Glucose.*
See http://en.wikipedia.org/wiki/Peptide_bond.*
See http://en.wikipedia.org/wiki/Ascorbic_acid.*
See http://en.wikipedia.org/wiki/Steroids.*
Zhang et al., "A new peptide-based urethane polymer: synthesis, biodegradation, and potential to support cell growth in vitro," (2000), Biomolecules 21, 1247-1258.*
Dieble et al., "Coating molecular barriers to acute platelet deposition on damaged arteries with reactive polyethylene glycol," J. Biomed. mater Res., 41, 251-56, 1998.*
"Organic Chemistry" by Wade, third edition, Prentice Hall Publishing, 1990, pp. 907-911.*
"Protein," Thomas E. Creeighton, 1996, Second Edition, W.H. Freeman and Company, pp. 4, 9, and 11.*
"Organic Chemistry" by Solomons, fifth edition, John Wiley and Sons, Inc., 1992, p. 820.*
International Patent Application Corresponding to Present US Application, International Search Report and Written Opinion.
Fano L, Ma Wy, Marcoli PA, Pizzi S, Fano V , "Polymerization of dental composite resins using plasma light", Biomaterials, 23 (4): 1011-1015 Feb. 2002.
Asmussen E, Peutzfeldt A, "Long-term fluoride release from a glass ionomer cement, a compomer, and from experimental resin composites", Acta Odontologica Scandinavica,60 (2): 93-97 Mar. 2002.
Sidhu Sk, Schmalz G, "The biocompatibility of glass-ionomer cement materials. A status report for the American Journal of Dentistry", American Journal of Dentistry, 14 (6): 387-396 Dec. 2001.
Christensen GJ, "Glass Ionomer-Resin—A Maturing Concept", Journal of the American Dental Association, 124 (7): 248-249 Jul. 1993.
Towler MR, Bushby AJ, Billington RW, Hill RG, "A preliminary comparison of the mechanical properties of chemically cured and ultrasonically cured glass ionomer cements, using nano-indentation techniques", Biomaterials, 22 (11): 1401-1406 Jun. 2001.
Braunwald NS, Gay W, Tatooles CJ, "Evaluation of crosslinked gelatin as a tissue adhesive and hemostatic agent: An experimental study", Surgery,59 (6): 1024-1030 Jun. 1966.
Tatooles CJ, Braunwald NS, "The use of crosslinked gelatin as a tissue adhesive to control hemorrhage from liver and kidney", Surgery, 60 (4): 857-861 Oct. 1966.

Ennker J, et al., "The impact of gelatin-resorcinol glue on aortic tissue: A histomorphologic evaluation", Journal of Vascular Surgery, 20 (1): 34-43 Jul. 1994.
Jackson MR, "Fibrin sealants in surgical practice: an overview", The American Journal of Surgery, 182 (2): S1-S7 Aug. 2001.
Velada JL, et al., "Reproducibility of the mechanical properties of Vivostat system patient-derived fibrin sealant", Biomaterials, 23 (10): 2249-2254 May 2002.
Seifman BD, Rubin MA, Williams AL, Wolf JS, "Use of absorbable cyanoacrylate glue to repair an open cystotomy", The Journal of Urology, 167: 1872-1875 Apr. 2002.
Lin JC, Lin CW, Lin X, "In vitro and in vivo studies for modified ethyl cyanoacrylate regimens for sclerotherapy", Journal of Biomedical Material Research, 53 (6): 799-805 Dec. 2000.
Marcovich R, Williams AL, Rubin MA, et al, "Comparison of 2-octyl cyanoacrylate adhesive, fibrin glue, and suturing for wound closure in the porcine urinary tract", Urology,57: 806-810, 2001.
Groot, J.H. et. al. "New Biomedical Polyurethane Ureas with High Tear Strength". Polymer Bulletin, vol. 38, No. 2, Feb. 1997, 211-218.
Cooper, C.W. and Falb, R.D.; "Surgical Adhesive", Ann NY Acad. Sci., Jan. 1968, 146(1):214-224.
Smith, D.C.; "Medical and Dental Applications of Cements", Journal of Biomed. Mater. Res. Symp., 1: 189-205 (1971).
Tseng Y-C, et al., "In Vivo Evaluation of 2-Cyanoacrylates as Surgical Adhesives," J. Appl. Biomater, 1990, 1 (2), 111-119.
Kobayashi H., et al., "Water-Curable and Biodegradable Prepolymer", J. Biomed. Mater. Res., 1991, 25, 1481-1494.
Matsuda T, et al., "A Novel Elastomeric Surgical Adhesive, Design Properties and In Vivo Performance," Trans. Am. Soc. Artif. Intern. Organ, 1986, 32, 151-156.
Matsuda T, et al., "Development of a Compliant Surgical Adhesive Derived from Novel Flurinated Hexamethylene Diisocyanate," Trans. Am. Soc. Artif. Intern. Organ;. 1989, 35, 381-383.
Toriumi D, "Surgical Tissue Adhesive: Host Tissue Response, Adhesive Strength and Clinical Performance," in Sierra D and Saits, R, ed. Surgical Adhesives and Sealants Current Technology and Applications, USA: Technomic, 1996: 61-69.

* cited by examiner

GLUCOSE

PEG

LYSINE DI-ISOCYANATE

LYSINE TRI-ISOCYANATE

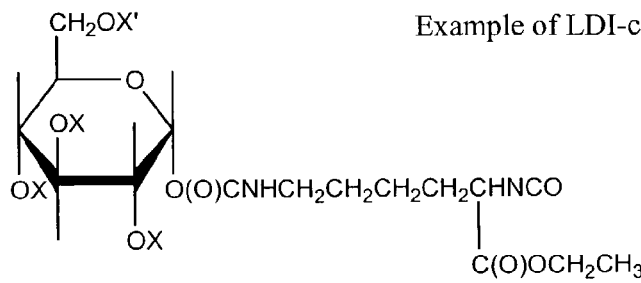
Example of LDI-capped glucose
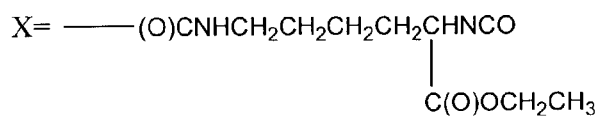
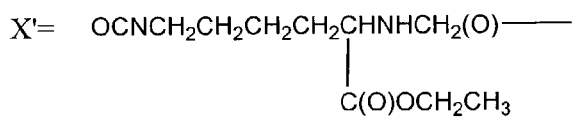
Fig. 3
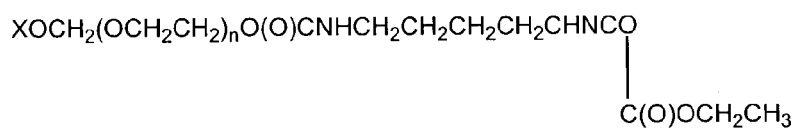
Example of LDI-capped PEG
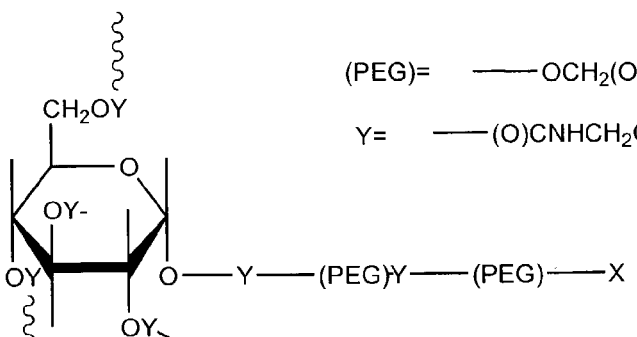
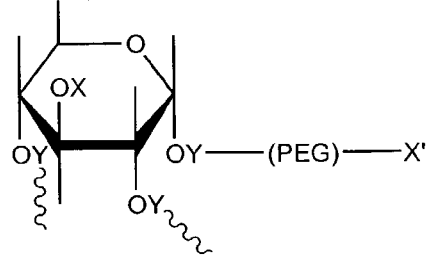
Example of a portion of a prepolymer of the present invention

MEDICAL ADHESIVE AND METHODS OF TISSUE ADHESION

CROSS-REFERENCE TO RELATED APPLICATION

This application claims the benefit of U.S. Provisional Patent Application Ser. No. 60/355,290, entitled MEDICAL ADHESIVE, filed Feb. 8, 2002, the disclosure of which is incorporated herein by reference.

BACKGROUND OF THE INVENTION

The present invention relates generally to medical adhesives and to methods of tissue closure, and, especially, to medical adhesives and to methods of tissue adhesion in which a mixture of isocyanate functional molecules or prepolymers is applied to tissue.

Each year approximately eleven million traumatic wounds are treated by emergency physicians in the United States. Traumatic wounds rival respiratory tract infections as the most common reason people seek medical care. Conventional methods of tissue closure (for example, sutures and staples) have several substantial limitations, including inability to produce fluid-tight closure, unsuitability for microsurgical applications, necessity for a second operation for removal, increased probability of inflammation and infection, and significant scarring and tissue injury during insertion. Medical tapes have been used for some applications, but medical tapes are limited by weak strength and problems with adherence to tissue. Treatment of lacerations with sutures often involves the injection of local anesthetic and use of needles, which can distress an already frightened patient. See, for example, McCaig L F, "National Hospital Ambulatory Medical Care Survey: 1992 Emergency Department Summary, *Vital Health Stat.*, 1994, 245, 1-12; and Eland J M, Anderson J E, "The Experience of Pain in Children," In: Jacox A K, ed. *Pain*, Boston, Mass.: Little Brown & Co., 1997 453-473. Suture wound repair is also painful and time-consuming. For quite some time, physicians have sought wound repair methods that require little time, do not require additional surgery, minimize the discomfort their patients, and produce a good cosmetic outcome.

In an attempt to achieve such goals, both biological and synthetic tissue adhesives have been developed. Applications of adhesives to biological tissue range from soft (connective) tissue adhesion to hard (calcified) tissue adhesion. Soft tissue adhesives are, for example, used both externally and internally for wound closure and sealing. Hard tissue adhesives are used, for example, to bond prosthetic materials to teeth and bone. Four main mechanisms of adhesion have been proposed for such tissue adhesives, including, mechanical interlocking, adsorption, diffusion theory, and electronic theory. Mechanical interlocking involves the penetration of the bonding agent into surface irregularities or porosity in the substrate surface as means for adhesion. Adsorption theory relies on the fact that if intimate interfacial molecular contact is achieved, interatomic and intermolecular forces will establish a strong joint. Diffusion theory states that the adhesion of polymers to substrates and each other requires mutual diffusion of polymer molecules or segments across the interface. Lastly, electronic theory suggests that electronic transfer between adhesive and adherent may lead to electrostatic forces that result in high intrinsic adhesion.

Unfortunately, currently available tissue adhesives have significant limitations. For example, biological tissue adhesives such as fibrin glues are effective in some uses, but are extremely expensive because they are derived from autologous tissue. Fibrin glue also suffers from relatively weak tensile strengths and labor-intensive means of production. Moreover, fibrinogen and thrombin obtained from human blood pose the risk of viral infection with, for example, acquired immune deficiency syndrome and/or hepatitis. See, for example, Spotniz W D, "History of Tissue Adhesives," in Sierra D, Saits R, editors, *Surgical Adhesives and Sealants, Current Technology and Applications*, USA: Technomic, 1996; and Borst A H, et al., "Fibrin Adhesive: An Important Hemostatic Adjunct in Cardiovascular Operations," *J. Thorac. Cardiovasc. Surg.*, 1982, 84, 548-553.

Synthetic and semi-synthetic surgical adhesives, such as cyanoacrylate, urethane prepolymers, and gelatin-resorcinol-formaldehyde, have also been proposed. See, for example, Tseng Y-C, et al., "In Vivo Evaluation of 2-cyanoacrylates as Surgical Adhesives," *J. Appl. Biomater,* 1990, 1, 11-22; Kobayashi H., et al., "Water-curable and Biodegradable Prepolymer, *J. Biomed. Mater. Res.*, 1991, 25, 1481-1494; Matsuda T, et al., "A Novel Elastic Surgical Adhesive, Design Properties and In Vivo Performance," *Trans. Am. Soc. Artif Intern. Organ,* 1986, 32, 151-156; and Matsuda T, et al., Department of a Compliant Surgical Adhesive Derived from Novel Flurinated Hexamethyiene Diisocyanate," *Trans. Am. Soc. Artif. Intern. Organ.,* 1989, 35, 381-383. However, these synthetic glues have several disadvantages including cytotoxicity, low degradation rates, and chronic inflammation induced by the sustained release of their degradation products (such as formaldehyde from cyanoacrylate polymers and gelatin-resorcinol-formaldehyde, and aromatic diamine from polyurethane). See, for example, Braumwald N S, et al., "Evaluation of Crosslinked Gelatin as a Tissue Adhesive and Hemostatic Agent: An Experimental Study," *Surgery,* 1966, 59, 1024-1030; and Toriumi D, "Surgical Tissue Adhesive: Host Tissue Response, Adhesive Strength and Clinical Performance," in Sierra D and Saits, R, ed. *Surgical Adhesives and Sealants Current Technology and Applications*, USA: Technomic, 1996: 61-69. Typically, synthetic glues are not suitable for internal use.

Cyanoacrylate macromonomers polymerize upon contact with water via chemistry similar to that used in well known "superglues". In addition to the problems set forth above, however, the use of the cyano-acrylate group in cyanoacrylate polymers limits the versatility of the formulation, and other functional groups in the material must be compatible with the hypersensitive cyanoacrylate. Use of acrylate-functional polyethylene glycols allows for sealing and degradation (upon incorporation of lactic acid or glycolic acid repeat units in the polyethylene glycol precursor). However, curing requires the use of UV or other radiation. Given the penetration depth limitations of the light, radiation cure limits the use of this technology to thin films that are readily accessible to the light source.

It is thus desirable to develop improved, adhesives and methods of tissue adhesion for use in connection with living tissue.

SUMMARY OF THE INVENTION

In one aspect, the present invention provides a method of applying an adhesive to organic tissue. The method includes the step of applying a mixture of molecules to the organic tissue. The mixture of molecules includes molecules having terminal isocyanate functional groups. The mixture of molecules has an average isocyanate functionality of at least 2.1 to enable crosslinking (or curing). More preferably, the average isocyanate functionality of the mixture is at least 2.5. The mixture of molecules preferably has a viscosity in the range of approximately 1 to approximately 100 centipoise to, for example, allow for ready application to tissue over a temperature range of use (typically, approximately 0° C. to approximately 40° C.). More preferably, the viscosity is in the range of approximately 1 to approximately 50 centipoise over a temperature range of use. In general, the mixture of molecules must be applicable or spreadable at the temperature of use.

The mixture of molecules forms a crosslinked polymer network or cures upon contact with the organic tissue in the presence of water. Sufficient water is generally present upon or within organic tissue and addition of water is not typically required for curing. The crosslinked polymer network is biocompatible and biodegradable. The crosslinked polymer network biodegrade into molecules or degradation products that are biocompatible.

Not all of the molecules of the mixture need to be stored in a mixed form. For example, mixing of molecules can occur just prior to application or during application.

In one embodiment, the mixture of molecules includes lysine tri-isocyanate or a lysine tri-isocyanate derivative (for example, lysine tri-isocyanate ethyl ester).

Preferably, the mixture of molecules includes isocyanate capped molecules formed by reacting multi-isocyanate functional molecules with multi-functional precursor molecules including terminal functional groups selected from the group consisting of a hydroxyl group, a primary amino group and a secondary amino group. As used herein, the term "multi-functional" refers to a compound that has two (di-functional) or more functionalities. Polyurethane prepolymers can thereby be formed. The multi-functional precursor compounds are biocompatible. Moreover, multi-amine functional precursors of the multi-isocyanate functional molecules are also biocompatible. The multi-amine functional precursors of the multi-isocyanate functional molecules can, for example, be biocompatible amino acids or biocompatible derivatives of amino acids. The multi-functional precursor molecules can, for example, include at least one of polyethylene glycol, a polyamino acid (typically, greater than 50 linked amino acids and including, for example, proteins and/or polypeptides), an aliphatic polyester (including, for example, polylactic acid, polyglycolic acid and/or polycaprolactone), a saccharide (including, for example, a sugar), a polysaccharide (for example, starch), an aliphatic polycarbonate, a polyanhydride, a steroid (for example, hydrocortisone), glycerol, ascorbic acid, an amino acid (for example, lysine, tyrosine, serine, and/or tryptophan), or a peptide (typically, 2 to 50 linked amino acids).

In one embodiment, the multi-functional precursor molecules include polyethylene glycol and the multi-isocyanate functional molecules include at least one of lysine di-isocyanate ethyl ester or lysine tri-isocyanate ethyl ester. The multi-functional precursor molecules can further include a sugar such as glucose.

In the case that the multi-functional precursor molecule include polyethylene glycol, the polyethylene glycol preferably has number average molecular weight less than 10,000. More preferably, the polyethylene glycol has number average molecular weight less than 2,000. Most preferably, the polyethylene glycol has number average molecular weight less than 1,000. In several embodiments of the present invention, the polyethylene glycol has a number average molecular weight in the range of approximately 50 to approximatelyn 1000.

Preferably, the mixture of molecules of the present invention forms a crosslinked polymer network in less than two minutes. More preferably, the mixture of molecules forms a cross-linked polymer network in less than one minute. The crosslinked polymer network resulting from curing of the mixture of molecules of the present invention upon contact with organic tissue preferably biodegrades in a period of time during which healing occurs. For example, the crosslinked polymer network preferably retains intact to adhere the tissue of a laceration or an incision until healing has sufficiently progressed that the wound or incision remains closed. In one embodiment, for example, the crosslinked polymer network biodegrades to lose at least approximately ⅔ of its material in approximately 7 to approximately 30 days, and, more preferably in approximately 7 to approximately 14 days.

In another aspect, the present invention provides an adhesive including a mixture of isocyanate capped molecules formed by reacting multi-isocyanate functional molecules with multi-functional precursor molecules including terminal functional groups selected from the group consisting of a hydroxyl group, a primary amino group and a secondary amino group. Preferably, the functional groups are hydroxyl groups. The multi-functional precursor compounds are biocompatible. Multi-amine functional precursors of the multi-isocyanate functional molecules are also biocompatible. As discussed, above, the mixture of molecules preferably has an average isocyanate functionality of at least 2.1 and, more preferably, has an average isocyanate functionality of at least 2.5. As also described above, the mixture of molecules preferably has a viscosity in the range of approximately 1 to approximately 100 centipoise. The mixture of molecules forms a crosslinked polymer network upon contact with the organic tissue in the presence of water. The crosslinked polymer network is biocompatible and biodegradable. The crosslinked polymer network degrades into degradation products including the precursor molecules and the multi-amine functional precursors.

In still another aspect, the present invention provides an adhesive including a mixture of isocyanate capped prepolymers formed by reacting multi-isocyanate functional molecules with multi-functional precursor molecules including terminal functional groups selected from the group consisting of a hydroxyl group, a primary amino group and a secondary amino group. Once again, the multi-functional precursor compounds are biocompatible. Also, multi-amine functional precursors of the multi-isocyanate functional molecules are biocompatible. At least one of the multi-functional precursors is a flexible biocompatible polymer having a number average molecular weigh of at least 50. As described above, the mixture of prepolymers has an average isocyanate functionality of at least 2.1. The mixture of prepolymer is a non-solid that is preferably spreadable for application to tissue over the temperature range of use. The mixture of prepolymers forms a crosslinked polymer network upon contact with the organic tissue in the presence of water. The crosslinked polymer network is biocompatible and biodegradable. The crosslinked polymer network degrades into degradation products including the precursor molecules and the multi-amine functional precursors.

In addition to other mechanisms of bonding to tissue as described above, the adhesives of the present invention present the possibility of chemically (covalently) bonding to the tissue. For example, reactive isocyanate groups on the adhesive can react with reactive groups such as hydroxyl groups or free amine groups in the tissue to form a covalent bond (that is, a urethane bond or a urea bond). The isocyanate groups also form a crosslinked polymeric network in the presence of moisture inherently present in and on tissue.

As discussed above, the adhesives of the present invention, the biodegradable crosslinked polymer network formed therefrom and the biodegradation products of that polymer network are preferably biocompatible. As used herein, the term "biodegradable" refers generally to the ability of the adhesive to be broken down (especially into innocuous degradation products) over time in the environment of use. As used herein, the term "biocompatible" refers generally to compatibility with living tissue or a living system. In that regard, the adhesives, polymer networks and degradation products of the present invention are preferably substantially nontoxic and/or substantially non-injurious to the living tissue or living system in the amounts required over the period of contact/exposure. Moreover, such materials preferably do not cause a substantial immunological reaction or rejection in the amounts required over the period of contact/exposure.

Unlike many currently available adhesives used in the medical arts for tissue closure and other uses, the adhesives of the present invention have relatively strong tensile strengths and form a relatively strong bond to tissue, while reducing or eliminating problems such as cytotoxicity, low degradation rates and inflammation associated with many current adhesives. The adhesives and methods of the present invention provide a minimally invasive avenue to, for example, tissue closure, with generally no mechanical damage to tissue and a decreased probability of infection. The adhesives of the present invention are relatively easy to synthesize and do not require the use of potentially harmful solvents In one embodiment, the present invention provides biocompatible and biodegradable lysine-di-isocyanate- (LDI-) or lysine-tri-isocyanate- (LTI-) based urethane polymers/prepolymers suitable for use as tissue adhesive. The LDI-polyurethane adhesives or glues are, for example, easily synthesized from LDI, polyethylene glycol (sometime referred to as PEG) and glucose without solvent. The degradation products are lysine, PEG, glucose and ethanol. The LDI-polyurethane tissue adhesives and other adhesives of the present invention reduce time required in wound repair, provided a flexible water-resistant protective coating and eliminate the necessity of suture removal. The LDI-polyurethane tissue adhesives and other tissue adhesives of the present invention are relatively easy to use following appropriate and common wound preparation as compared to currently available skin adhesives. The adhesives of the present invention are more convenient to use than conventional repair methods such a suture because, for example, patients, and especially children, are more likely to accept the idea of being "glued" over such conventional or traditional methods of repair.

Furthermore the modulus or stiffness of the LDI-based polyurethane tissue adhesives and other tissue adhesives of the present invention can be readily adjusted for use either as soft (connective) tissue adhesives (for example, as skin adhesives to replace sutures and staples for closure of certain lacerations and/or incisions) and as hard (calcified) tissue adhesives (for example, as bone or dental adhesives) in both humans and animals.

BRIEF DESCRIPTION OF THE DRAWINGS

FIG. 3 illustrates examples of the chemical structure of LDI capped glucose, LDI capped polyethylene glycol and a LDI capped LID-PEG-glucose prepolymer.

DETAILED DESCRIPTION OF THE INVENTION

A tissue adhesive is preferably a liquid or in another spreadable form (for example, a fluid-like gel) for application to the tissue. The adhesive also preferably solidifies relatively quickly when applied and binds to living tissues in the presence of moisture. The tissue adhesive is also preferably nonirritating locally and nontoxic systematically in the amount required to achieve an effective tissue adhesion. In addition, appropriate flexibility and degradability are required for the cured adhesive in, for example, wound closure so the adhesive does not disturb healing. The tissue adhesives of the present invention satisfy those criteria.

Figure 1:
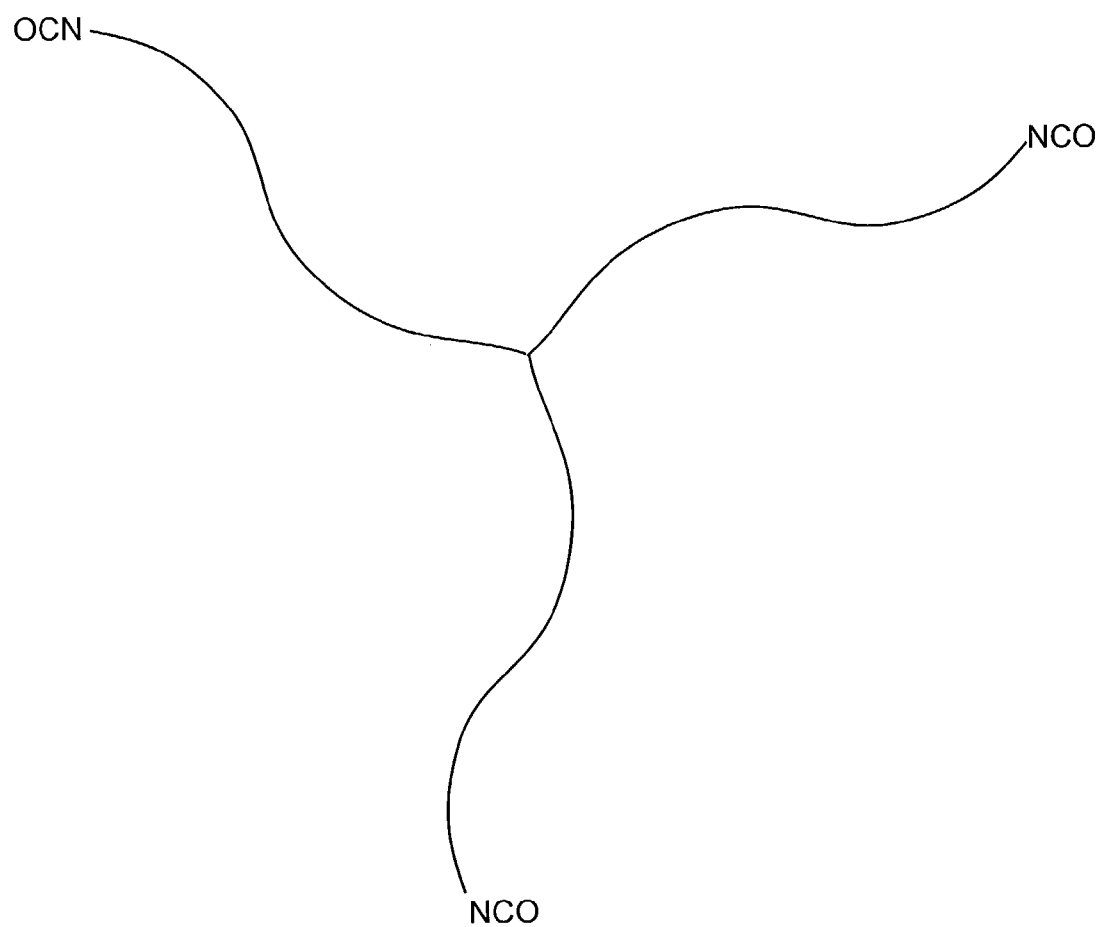
FIG. 1 illustrates the general structure of a isocyanate capped prepolymer of the present invention.

In general, the adhesives of the present invention include a mixture of molecules having terminal isocyanate functional groups. The mixture of molecules has an average isocyanate functionality of greater than 2 (per molecule or chain), and preferably greater than 2.1 to enable crosslinking (or curing). More preferably, the average isocyanate functionality of the mixture is at least 2.5. Although it is possible to use relatively low molecular weight molecules such as lysine tri-isocyanate or a combination of lysine di-iscoyanate and tri-isocyanate as an adhesive of the present invention, the adhesives of the present invention are preferably applied as a mixture of isocyanate capped polymers/prepolymers. A general depiction of an example of such a molecule is illustrated in FIG. 1. Such prepolymers can, for example, be formed by reacting multi-isocyanate functional molecules with multi-functional precursor molecules including terminal functional groups selected from the group consisting of a hydroxyl group, a primary amino group and a secondary amino group. Preferably, the functional groups are hydroxyl groups.

As discussed above, the isocyanate caps of a molecule such as represented in FIG. 1 enable crosslinking and may enhance adhesion to tissue by covalently bonding to hydroxyl groups and amine groups in the tissue. The precursor compounds which react with multi-isocyanate functional molecules to form the "middle" or interior chain section(s) of such molecules are preferably chosen to enable control of physical properties such as the viscosity of the adhesive and the elasticity of the cured polymer network.

For example, the physical properties of the cured polymer network can be controlled by the overall or average functionality of the adhesive (average number of isocyanate end groups per chain), the molecular weight between crosslinks (that is, the molecular weight between isocyanate groups in the prepolymer), the aromatic content of the prepolymer for certain prepolymers including aromatic groups (incorporated, for example, through addition of the biocompatible amino acid tyrosine), and the number of hydrogen bonding groups (for example, urea groups and urethane groups) in the prepolymer. For example, increasing the functionality (through, for example, use of higher quantities of an isocyanate-capped sugar in the precursor) leads to a crosslinked polymer network with relatively higher modulus (stiffness). Increasing the molecular weight between crosslink points (by for example, incorporating a PEG "spacer" of higher molecular weight), decreasing the number of hydrogen bonding groups, or decreasing aromatic content decreases the modulus of the crosslinked polymer networks formed by the adhesives of the present invention. Hence, one can regulate the properties of the adhesive bond over a wide range through known modifications to the original formulation.

Biocompatible compounds or molecules chosen for the middle or interior chain sections can also be chosen to impart other desirable properties to the adhesives. For example, an active enzyme (protein) can be incorporated to, for example, inhibit a particular bacteria or enhance a particular biological function. It has previously been shown that addition of an aqueous solution of protein to a urethane prepolymer prompts incorporation of the protein (covalently) into the polyurethane network (via reaction of free amines on the protein with the terminal isocyanate groups). Such incorporation preserves the activity of the protein while increasing the stability by several orders of magnitude. Likewise, a steroid such as hydrocortisone (which has been incorporated into an adhesive of the present invention) can be incorporated to act as, for example, an anti-inflammatory.

Figure 2:
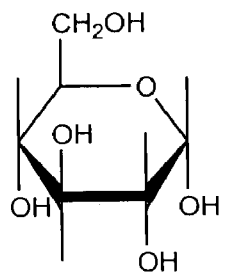
FIG. 2 illustrates the chemical structures of lysine di-isocyanate (LDI), lysine tri-isocyanate (LTI), polyethylene glycol (PEG) and glucose.
Figure 2:
Figure 2:
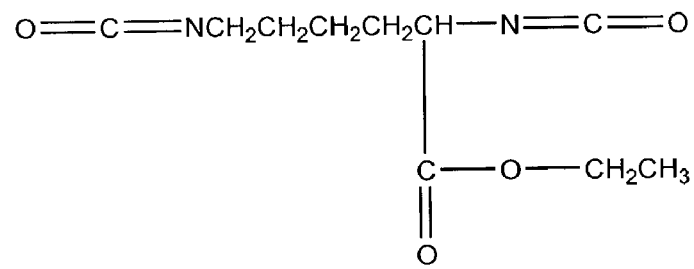
Figure 2:
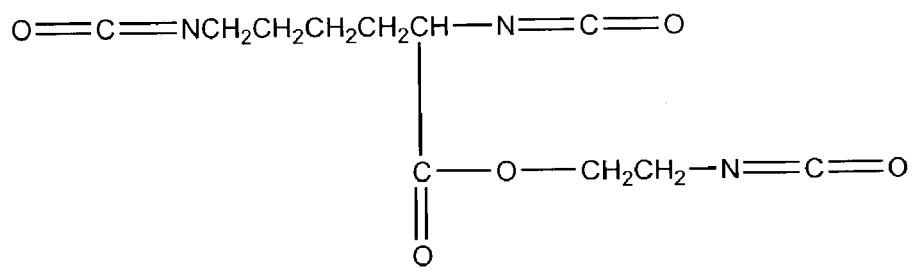

To illustrate the present invention, studies of representative adhesives including an isocyanate functional prepolymer generated from the following molecules or building blocks are set forth: lysine di-isocyanate ethyl ester or LDI (synthesized via the phosgenation of the ethyl ester of lysine) or lysine tri-isocyanate LTI; glucose (including five hydroxyl functional groups) and polyethylene glycol or PEG (including two hydroxyl function groups). The isocyanate groups of the LDI or LTI form prepolymer chain via reaction with the hydroxyl groups of the glucose and the PEG. Use of an excess of LDI or LTI helps to ensure that substantially all or all hydroxyl group react with isocyanate resulting in an isocyanate-capped prepolymer. The chemical structures of the molecular building blocks used in the studies of the present invention are set forth in FIG. 2. FIG. 3 illustrates representative examples of isocyanate- (LDI-) capped glucose, isocyanate- (LDI-) capped PEG and an isocyanate- (LDI-) capped PEG-glucose-LDI prepolymer molecule. Lysine di-isocyanate, which is a volatile compound, is rendered non-volatile through incorporation into the polymeric precursors of the present invention (hence, LDI is not present, but is rather locked into a macromonomer).

The adhesive is thus simply a polyurethane prepolymer, that is, a polyurethane precursor where all reactive end groups (amine and hydroxyl) have been capped with, for example, lysine di-isocyanate, leaving numerous terminal isocyanate groups and preferably little or no free hydroxyl or amine groups (to prevent further reaction) in the prepolymer. Exposure of such a prepolymer to tissue can result in covalent bonding of the polymer to the tissue through the reaction of free amine groups or hydroxyl groups with the isocyanate groups in the prepolymer. Further, water will also react with the isocyanate groups, liberating $CO_2$ and forming additional free amine groups, which ultimately react with isocyanates to form crosslink points.

In general, the number of crosslinking points was controlled primarily via the concentration of glucose, which includes five hydroxyl groups. Using a relatively high concentration of glucose increases crosslinking points and increases the modulus of the crosslinked polymer network. A biocompatible, generally flexible polymer such as PEG acts, in part, as a spacer. Increasing the molecular weight of the PEG used in the adhesives of the present invention increases the distance between crosslinking points and decreases the modulus of the crosslinked polymer network Unlike the adhesives of the present invention, commercial polyurethanes (including adhesives) are generated from aromatic isocyanates. Their rate of degradation is not sufficiently fast for use in-vivo (as biodegradable adhesives) and the byproducts of degradation of commercially available polyurethane adhesives include toxic aromatic diamines.

Lysine di-isocyanate was generated via phosgenation of the ethyl ester of lysine in the presence of pyridine. Unlike lysine or its ethyl ester, LDI is volatile and hence is readily purified via distillation at reduced pressure.

Several studies have indicated the biocompatibility and biodegradability of LDI-based polymers. For example, polymer foams were created via addition of water to a glycerol/LDI prepolymer. The prepolymer was generated via the capping of each of the three hydroxyl groups in glycerol with LDI. Degradation of the foams occurred over a time period of weeks, with a loss of ⅔ of the material after 60 days. Degradation products were measured as primarily lysine and glycerol. Those materials thus degraded significantly faster than conventional polyurethanes. Possibly, the ester group (from lysine) activates the urethane linkage to hydrolysis. Further, the ester group, once hydrolyzed, acts as an in-situ acid catalyst to speed hydrolysis of the urethane linkages. Bone marrow stromal cells (BSMC's) from New Zealand white rabbits were seeded on the glycerol/LDI foams, and were observed to adhere and spread. BMSC's produced collagen (as found through measurement of hydroxy proline) at levels commensurate with control cells.

Further studies were performed using glucose/LDI foams. In such studies, LDI was added to glucose in a 5:2 ratio. Addition of water created a rigid (high modulus) foamed material. By withdrawing prepolymer samples prior to completion of the LDI+glucose reaction, foams could be created that were soft and flexible. As in previous studies, BMSC's were seeded on these foams. The BMSC's both adhered to the foam and spread thereon. Glucose-LDI foams degraded to sugar and lysine over a period of 2 to 3 months, depending upon the crosslink density of the materials (i.e., soft foams degraded more quickly that more rigid foams). Furthermore, small samples of glucose-LDI foams were implanted in New Zealand white rabbits. Samples of the material and surrounding tissue were removed after two months. Fewer giant cells, for example, were observed in these samples than in control samples using polylactic acid/glycolic acid copolymers.

The polymeric foams described above were generally highly crosslinked materials. Once formed, these materials could not be reprocessed. Linear polymers from LDI and di-functional polyethylene glycols (molecular weights from 200 to 8000) were also synthesized. While such polymer were processable, the polymers dissolved in water. Extension of the "hard" segment of those polyurethanes to produce thermoplastic elastomers (i.e., processable yet water-insoluble polymers) was accomplished via the use of tyrosine, lysine, or tryptophan as chain extenders. In such studies, an excess < of LDI was added to the other amino acid. The resulting LDI-amino acid-LDI compound was then reacted with the polyethylene glycol) The use of the chain extended hard segment allowed generation of processable polyurethanes from LDI that did not dissolve in water.

Figure 4A:
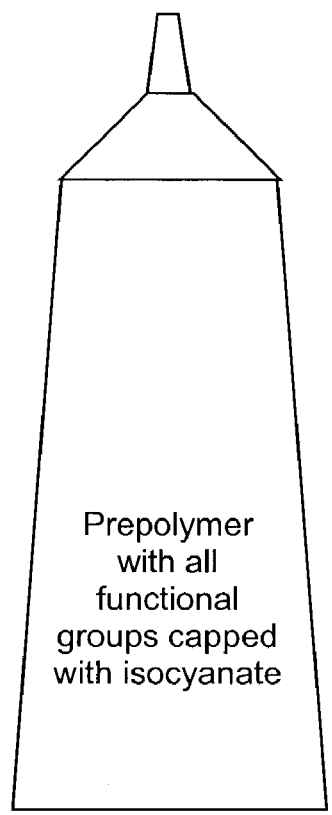
FIG. 4A illustrates a container encompassing an adhesive of the present invention in which substantially all or all of the functional groups of the molecules of the adhesive are capped with isocyanate functionality.
Figure 4B:
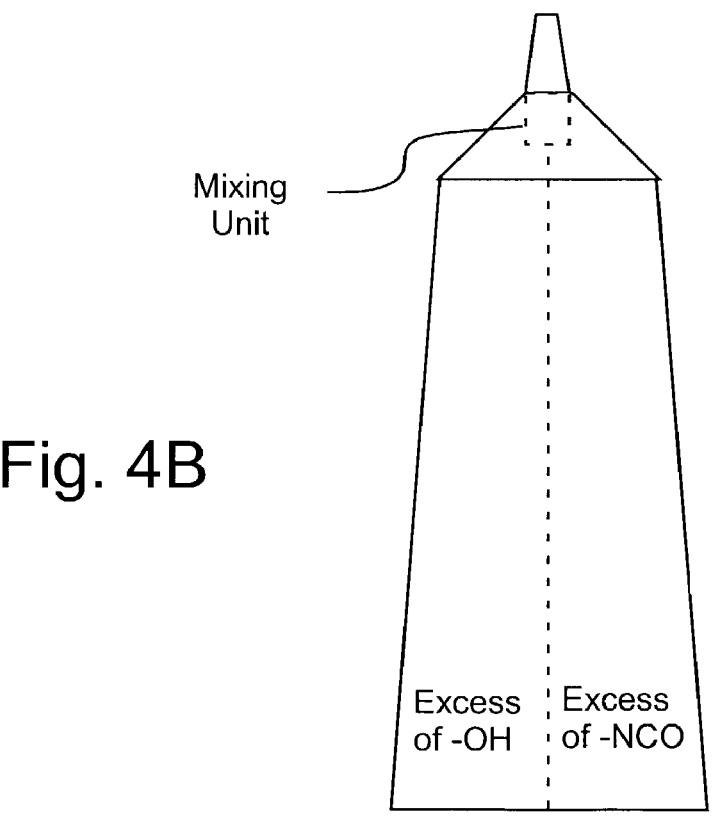
FIG. 4B illustrates a dual-compartment container in which one compartment includes a mixture of molecules/prepolymers having an excess of hydroxyl (and/or amine) functionality and the other compartment includes a mixture of molecules/prepolymers having an excess of isocyanate (—NCO) functionality.

The crosslinked materials described above are generally not preferred for use as adhesives although they can be applied as such in the manner described in connection with FIG. 4B below. Nonetheless, the above studies indicated that (a) isocyanate-terminal prepolymers are readily synthesized, (b) polymer foams generated from LDI and either glucose or glycerol degrade over a period of 2-3 months, generating primarily lysine and the hydroxy-functional precursor, (c) bone marrow stromal cells readily attach and thrive on polymer foams generated from LDI, (d) LDI-glucose polymers produce a mild immune reaction in-vivo.

Preferred embodiments of the adhesives of the present invention include mixtures of isocyanate capped prepolymers that are suitably functionalized to crosslink upon application to tissue as described above. To achieve a spreadable adhesive that cures to a water-resistant biodegradable and biocompatible polymer network, a prepolymer can incorporate a multi-isocyanate functional molecule such as LDI or LTI as described above, a molecule such as glycerol or a sugar that is relatively highly functionalize (having at least three reactive functional groups) to create crosslink points, and a spacer molecule/group such as PEG which must be at least di-functional for incorporation into the interior chain of the prepolymer. The spacer is preferably a polymer of a number average molecular weight of at least 50 that, when increased in concentration relative to the other components of the prepolymer, acts to lower the viscosity of the adhesive and/or to decrease the modulus of the cured polymer network.

Preferably, substantially all or all of the functional groups of the molecules of the adhesive are capped/functionalized with iscyanate functionality to prevent further reaction. In that regard, at least a stoichimetric amount of isocyanate functionality and, preferably, an excess of isocyanate functionality is used durning synthesis. As illustrated in FIG. 4A, such an adhesive of the present invention (in which substantially all or all of the functional groups of the molecules of the adhesive are capped with isocyanate functionality) can be stored in a water-tight container in the absence of water for extended periods of time until application. As illustrated in FIG. 4B, extended storage can also be achieved using a dual-compartment container in which one compartment includes a mixture of molecules/prepolymers having an excess of hydroxyl (and/or amine) functionality and the other compartment includes a mixture of molecules/prepolymers having an excess of isocyanate (—NCO) functionality. The container can include a mixing unit or element as known in the art to mix the contents of each compartment upon application to tissue to create a crosslinked polymer network.

EXAMPLE 1

A representative LDI-based polyurethane tissue adhesive or glue was synthesized using the procedure described below. To generate the adhesive, 0.5889 gram glucose (3.27 mmol, —OH 16.36 mmol) was added to 5 ml of PEG 400 (14.09 mmol, —OH 28.18 mmol) in a dry round-bottomed flask, flushed with nitrogen and heated at 50° C. to make a clear solution. PEG is a liquid at room temperature and solubilized the glucose without the need for additional solvent. Subsequently, 4.6 ml of lysine di-isocyanate (LDI, d 1.157, FW 226, 23.55 mmol, —NCO 47.10 mmol) was added, and the flask was fitted with a rubber septa and sealed. The reaction mixture was stirred at 50° C. for 48 hr, and a viscous solution was obtained. The viscous solution was kept at room temperature under nitrogen until use. The viscous liquid was spread onto each of two pieces of moist tissue, which when pressed together would adhere firmly to each other after approximately 1-2 minutes.

EXAMPLE 2

Another LDI-based polyurethane tissue was synthesized by the following procedure using PEG 200 rather than PEG 400, which ultimately generated a seal that was stiffer and exhibited greater strength than the adhesive of Example 1. In this procedure, 0.6 gram glucose (3 mmol, —OH 15 mmol) was added to 5 ml of PEG 200 (28.18 mmol, —OH 56.35 mmol) in a dry round-bottomed flask, flushed with nitrogen and heated at 50° C. to make a clear solution. Subsequently, 7 ml of LDI (d 1.157, FW 226, 35.83 mmol, —NCO 71.67 mmol) was added, and the flask was fitted with a rubber septa and sealed. The reaction mixture was stirred at 50° C. for 48 hr, and a viscous solution was obtained. The glue was kept at room temperature under nitrogen until use. The viscous liquid was spread onto each of two pieces of moist tissue, which when pressed together adhered firmly to each other after 1-2 minutes.

EXAMPLE 3

Example 3 illustrated that when the portion of glucose was increased in the reaction mixture, the time needed for closing the wound was shorter, the bond strength increased, and the ultimate material was stiffer. In this study, 1.8 gram glucose (10 mmol, —OH 50 mmol) was added to 5 ml of PEG 200 (28.18 mmol, —OH 56.35 mmol) in a dry round-bottomed flask, flushed with nitrogen and heated at 50° C. to make a clear solution. Subsequently, 10 ml of LDI (d 1.157, FW 226, 51.19 mmol, —NCO 102.02 mmol) was added. The flask was fitted with a rubber septa and sealed. The reaction mixture was stirred at 50° C. for 48 hr, and a viscous solution was obtained. The glue was kept at room temperature under nitrogen until use. The viscous liquid was spread onto each of two pieces of moist tissue, which when pressed together would adhere firmly to each other after approximately 1 minute

EXAMPLE 4

In this study, the procedure of Example 3 was generally followed, except that the study substituted PEG 200 with PEG 400. In this study, 1.8 gram glucose (10 mmol, —OH 50 mmol) was added in 10 ml of PEG 400 (28.18 mmol, —OH 56.35 mmol) in a dry round-bottomed flask, flushed with nitrogen and heated at 50° C. to make a clear solution. Subsequently, 10 ml of LDI (d 1.157, FW 226, 51.19 mmol, —NCO 102.39 mmol) was added, and the flask was fitted with a rubber septa and sealed. The reaction mixture was stirred at 50° C. for 48 hr, and a viscous solution was obtained. The solution was kept at room temperature under nitrogen until use. The viscous liquid was spread onto each of two pieces of moist tissue, which when pressed together adhered firmly to each other after approximately 1 minute.

EXAMPLE 5

In this study, lysine tri-isocyanate was substitued for lysine di-isocyanate. Lysine tri-isocyanate can be obtained commercially, or synthesized via (a) generating the aminoamide derivative of lysine via the coupling of ethylene diamine (large excess) to lysine using any one of a number of carbodiimides, followed by (b) phosgenation. When LTI (lysine tri-isocyanate) instead of LDI is reacted with glucose and PEG, the set-up time of the material was much shorter (only 30 seconds), and the bond strength was much stronger. In the study of this Example, 0.6 gram glucose (3.33 mmol, —OH 16.67 mmol) was added in 5 ml of PEG 200 (28.18 mmol, —OH 56.35 mmol) in a dry round-bottomed flask, flushed with nitrogen and heated at 50° C. to make a clear solution. Subsequently, 5 ml of LTI (d 1.231, FW 267.25, 23.05 mmol, —NCO 69.15 mmol) and was added, and the flask was fitted with a rubber septa and sealed. The reaction mixture was stirred at 50° C. for 48 hr, and a viscous solution was obtained. The solution was kept it at room temperature under nitrogen until use. The viscous liquid was spread onto each of two pieces of moist tissue, which when pressed together adhered firmly to each other after 30 seconds.

EXAMPLE 6

In this example, the procedure of Example 5 was generally follwed, exepet that PEG 400 (instead of PEG 200) was reacted with LTI. In this study, the material set-up time was the same as that of LTI-glucose-PEG 200. Here, 0.229 gram glucose (1.27 mmol, —OH 6.36 mmol) was added in 5 ml of PEG 400 (14.1 mmol, —OH 28.2 mmol) in a dry round-bottomed flask, flushed with nitrogen and heated at 50° C. to make a clear solution. Subsequently, 2.5 ml of LTI (d 1.231, FW 267.25, 11.52 mmol, —NCO 34.55 mmol) was added, and the flask was fitted with a rubber septa and sealed. The reaction mixture was stirred at 50° C. for 48 hr, and a viscous solution was obtained. The viscous solution was kept at room temperature under nitrogen until use. The viscous liquid was spread onto each of two pieces of moist tissue, which when pressed together adhered firmly to each other after 30 seconds.

EXAMPLE 7

In this example, two precursor solutions were prepared, then mixed just prior to application to moist tissue. Solution A was made from 2.15 g PEG 200 (10.75 mmol, —OH 21.5 mmol) and 4.4 ml of LDI (d 1.157, FW 226, 22.53 mmol, —NCO 45.05 mmol) after 48 hr of reaction. Solution B was made from 4.2 g PEG 200 (21 mmol, —OH 42 mmol) and 2.2 ml of LDI (11.26 mmol —NCO 22.52 mmol) after 48 hr of reaction. Because solution A had excess LDI in the reaction moxture, and solution B had excess PEG 200 in the reaction mixture, both A and B solutions could be stored for long periods of time. The same volume of each solution was mixed well to use as a glue. Once the A and B solutions were mixed thoroughly (1:1 ratio by volume), the viscous liquid was spread onto each of two pieces of moist tissue. When pressed together, the tissue pieces adhered firmly to each other after 2 minutes.

EXAMPLE 8

In this example two precursor solutions were again prepared, then mixed just prior to application to moist tissue. Solution A was made from 4 g PEG 400 (10 mmol, —OH 20 mmol) and 4 ml of LDI (d 1.157, FW 226, 20.48 mmol, —NCO 40.96 mmol) after 48 hr of reaction. Solution B was made from 8 g PEG 400 (20 mmol, —OH 40 mmol) and 2 ml of LDI (10.23 mmol —NCO 20.48 mmol) after 48 hr of reaction. Because solution A had excess LDI in the reaction mixture, and solution B had excess PEG 400 in the reaction mixture, both solutions A and B were easy to store for long periods of time. The same volume of each solution was mixed well to use as glue. Once the A and B solutions were mixed thoroughly (1:1 ratio by volume), the viscous liquid was spread onto each of two pieces of moist tissue. When pressed together, the pieces of tissue adhered firmly to each other after 2 minutes.

EXAMPLE 9

In this example two precursor solutions were again prepared, then mixed just prior to application to moist tissue. Solution A was made from 0.9 g glucose (5 mmol, 25 mmol —OH) to 5 ml of PEG 200 (28.18 mmol, —OH 56.35 mmol, total —OH 81.35 mmol) and 16 ml of LDI (d 1.157, FW 226, 81.9 mmol, —NCO 163.82 mmol) after 48 hr of reaction. Solution B was made from 1.8 g glucose (10 mmol, —OH 50 mmol) in 10 ml of PEG 200 (56.35 mmol, —OH 112.7 mmol, total —OH 162.7 mmol) and 8 ml of LDI (40.96 mmol —NCO 81.91 mmol) after 48 hr of reaction. Because solution A had excess —NCO in the reaction mixture, and solution B had excess —OH in the reaction mixture, both solutions A and B were easy to store for long periods of time. The same volume of each solution was mixed well to use as skin glue. Once the A and B solutions were mixed thoroughly (1:1 ratio by volume), the viscous liquid was spread onto each of two pieces of moist tissue. When pressed together the tissue pieces adhered firmly to each other after approximately 2 minutes.

EXAMPLE 10

In this example, gelatin was used with an LDI-polyurethane adhesive of the present invention. The set-up or cure time was found to be shorter than when the LDI-based polyurethane adhesive was used without gelatin. In this study, 100 µl of 0.1% gelatin (Type A: from porcine skin, 300 bloom, Sigma Co.) was mixed with 0.5 ml of the LDI-based polyurethane from Example 1. This viscous liquid was spread onto each of two pieces of moist tissue, which when pressed together adhered firmly to each other after approximately 10-30 seconds.

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method comprising applying a moisture-curable, isocyanate-functional adhesive to tissue, the adhesive comprising the reaction product of a reaction mixture consisting essentially of:
   (a) a stoichiometric excess of an isocyanate reactant selected from the group consisting of lysine tri-isocyanate, lysine di-isocyanate, lysine di-isocyanate ethyl ester, and combinations thereof; and
   (b) a multi-functional reactant selected from the group consisting of a saccharide, a polysaccharide, a steroid, glycerol, ascorbic acid, an amino acid, and combinations thereof, the multi-functional reactant having at least two isocyanate-reactive functional groups,
   wherein the reaction product has an average isocyanate functionality of at least 2.1 and forms covalent bonds upon application to tissue.

2. The method of claim 1 wherein the average isocyanate functionality of the reaction product is at least 2.5.

3. The method of claim 1 wherein the multi-functional reactant comprises a saccharide.

4. The method of claim 3 wherein the saccharide comprises glucose.

5. The method of claim 1 wherein the multi-functional reactant comprises glycerol.

6. The method of claim 1 wherein the multi-functional reactant is selected from the group consisting of a saccharide, glycerol, and combinations thereof.

* * * * *